United States Patent [19]

Ducheyne et al.

[11] Patent Number: 4,990,163
[45] Date of Patent: Feb. 5, 1991

[54] METHOD OF DEPOSITING CALCIUM PHOSPHATE CERMAMICS FOR BONE TISSUE CALCIFICATION ENHANCEMENT

[75] Inventors: Paul Ducheyne, Bryn Mawr; John Cuckler, Haverford, both of Pa.; Shulamit Radin, Cherry Hill, N.J.

[73] Assignee: Trustees of the University of Pennsylvania, Philadelphia, Pa.

[21] Appl. No.: 307,326

[22] Filed: Feb. 6, 1989

[51] Int. Cl.⁵ ............................................. A61F 2/28
[52] U.S. Cl. ...................................... 623/66; 623/16; 427/2
[58] Field of Search ............... 623/16, 66, 901; 427/2; 501/95

[56] References Cited

U.S. PATENT DOCUMENTS 4,308,064  12/1981  Takami et al. ..................... 623/16 X
4,863,475  9/1989  Andersen et al. ..................... 623/16

OTHER PUBLICATIONS

"Total Joint Replacement Arthroplasty without Cement", Galante, J. O., Guest Editor, Clin. Orthop. 176, Section I, Symposium, 24–34 (1983).
Morscher, E., "Cementless Total Hip Arthroplasty", Clin. Orthop. 181, 76–91 (1983).
Eftekhar, N. S., "Long-Term Results of Total Hip Arthroplasty", Clin. Orthop. 225, 207–217 (1987).
Hulbert, S. F., Young, F. A., et al., "Potential of Ceramic Materials as Permanently Implantable Skeletal Protheses", J. Biomed, Mater. Res. 4, 433–456 (1970).
Griss, P., Silber, R. et al., "Biomechanically Induced Tissue Reactions after Al₂O₃ . . . ", J. Biomed. Mater. Res. Symp. 7, 5191 ∝ 528 (1976).
Hench, L. L., Splinter, R. J., et al., "Bonding Mechanism at the Interface of Ceramic Prosthetic Materials", J. Biomed. Mater. Res. Symp. 2, 117–141 (1973).
Charnley, J., "Low-Friction Arthroplasty of the Hip", Springer-Verlag, Berlin, Heidelberg, New York (1979).
Ducheyne, P., "The Fixation of Permanent Implants: a Functional Assessment", Functional Behavior of Orthopedic Biomaterials, vol. II, CRC Press, Boca Ratan, Fla. (1984).
Gross, U., Schmitz, H. J. et al., "Surface Activities of Bioactive Glass . . . ", Ed. P. Ducheyne, J. Lemons, Ann. N.Y. Acad. Sci., 523 (1988).
R. LeGeros, et al., "Significance of the Porosity and Physical Chemistry of Calcium Phosphate Ceramics . . . ", Ed. P. Ducheyne, J. Lemons, Ann. N.Y. Acad. Sci., 523 (1988).
Ducheyne, P., Hench, L. L., "Comparison of the Skeletal Fixation of Porous and Bioactive Materials", Trans. 1st. Mtg., Europ. Soc. Biomater, p. 2, ps. 9/77, Strasbourg.
Ducheyne, P. et al., "The Effect of Hydroxyapatite Impregnation on Bonding of Porous Coated Implants", Trans. 5th Mtg. Biomat., p. 30 (1979).
Ducheyne, P. et al., "The Effect of Hydroxyapatite Impregnation on Skeletal Bonding of Porous Coated Implants", J. Biomed., Mater. Res. 14, 225–237 (1980).

(List continued on next page.)

Primary Examiner—Alan W. Cannon
Attorney, Agent, or Firm—Woodcock Washburn Kurtz Mackiewicz & Norris

[57] ABSTRACT

Improved ceramics which promote bone ingrowth are disclosed. The coating of the present invention consists essentially of oxyhydroxyapatite, and alpha- and beta-tricalcium phosphate. Methods of making and using the ceramics are also disclosed. The present invention uses a microscopically powdered form of calcium-phosphate materials and electrophoretic deposition to create ceramics having significantly higher dissolution rates than previous materials. By agitating the electrophoretic solution, agglomeration is prevented and a uniform coating is achieved. Thus, the present invention presents both improved ceramic materials and novel methods of depositing them uniformly upon metal surfaces, such as titanium wire mesh.

15 Claims, 2 Drawing Sheets

OTHER PUBLICATIONS

Berry, J. L., Geiger, J. M. et al., "Use of Tricalcium Phosphate or Electrical Stimulation to Enhance...", J. Biomed. Mater. Res. 20, 65–77 (1986).

Eschenroeder, H. C., McLaughlin, R. E., et al., "Enhanced Stabilization of Porous Coated Metal Implants...", Clin. Orthop. 216, 234–246 (1987).

Rivero, D. P., Fox, J. et al., "Calcium Phosphate Coated Porous Titanium Implants...", J. Biomed. Mater. Res. 22, 191–202 (1988).

Mayor, M. D., Collier, J. B., et al., "Enhanced Early Fixation of Porous Coated Implants Using Tricalcium Phosphates", Trans. 32nd ORS, 348 (1986).

Cook, S. D., Thomas, K. A., et al., "Hydroxyapatite-Coated Porous Titanium for Use...", Clin. Orthop. 230, 303–312 (1988).

Oonishi, H. et al., "Comparison of Bone Ingrowth into Ti–Ga1–4V Bends Coated and Uncoated with Hydroxyapetite", Trans. 3rd. World Biomat. Conf., Kyoto, P. 584 (1988).

Ducheyne, P. et al., "Bioactive Ceramic Coatings on Metal: Structure Property Relationships of Surfaces and Interfaces", Bioceramics 1988, Euramerica, Tokyo (1988 in press).

METHOD OF DEPOSITING CALCIUM PHOSPHATE CERMAMICS FOR BONE TISSUE CALCIFICATION ENHANCEMENT

FIELD OF THE INVENTION

The present invention relates to materials and processes which enhance bone ingrowth in porous surfaces, such as titanium implants. Specifically, materials and processes are presented which permit calcium phosphate ceramic materials to be uniformly deposited by electrophoresis.

BACKGROUND OF THE INVENTION

Bone tissue consists of approximately 60–67% by weight of calcium phosphate crystals finely dispersed in a collagenous matrix, and also contains about 10% water. Some bone-forming reactions have been described. However, neither the actual sequence nor the specific mechanisms leading to bone formation are fully understood. It is logical, however, to consider bone formation as the result of two major trains of events, i.e., a first one that produces the collagen precursor matrix; the next a sequence of steps that leads to calcification, i.e., the mineralization of the organic matrix. These two phases are distinct, since it is possible to microscopically distinguish the calcified tissue from the non-calcified (osteoid) tissue in bone tissue that is being laid down.

Cementless fixation of permanent implants has become a widespread surgical procedure which aids in avoiding some of the late complications of cemented prosthesis See, "Total joint replacement arthroplasty without cement", Galante, J. O., guest editor Clin. Orthop 176, section I, symposium, pages 2-114 (1983); Morscher, E., "Cementless total hip arthroplasty", Clin. Orthop. 181, 76–91 (1983); Eftekhar, N. S., "Long term results of total hip arthroplasty", Clin. Orthop. 225 207–217 (1987). In principle, cementless fixation can be achieved by using any of three methods: bone tissue ingrowth in porous coatings, bone tissue apposition on undulated, grooved, or surface structured prostheses, and fixation through chemical reaction with a bioactive implant surfaces See, Hulbert, S. F., Young, F. A., Mathews, R. S., Klawitter, J. J., Talbert, C. D., Stelling, F. H., "Potential of ceramic materials as permanently implantable skeletal prostheses", J. Biomed. Mater. Res. 4, 433–456 (1970); Griss, P., Silber, R., Merkle, B., Haehner, K., Heimke, G., Krempien, B., "Biomechanically induced tissue reactions after Al$_2$O$_3$-ceramic hip joint replacement Experimental study and early clinical results", J. Biomed Mater. Res. Symp. No. 7, 519–528 (1976); Hench, L. L., Splinter, R. J., Allen, W. C., Greenlee, T. K., Jr., "Bonding mechanisms at the interface of ceramic prosthetic materials", J. Biomed Mater. Res. Symp 2, 117–141 (1973). Common to these three principles of fixation is the necessity that the surrounding tissues establish and maintain a bond with the device. This can be contrasted with the cemented reconstructions of which failure is invariably associated with destruction or resorption of surrounding bone tissue. See, Charnley, J., "Low-friction arthroplasty of the hip", Springer-Verlag, Berlin, Heidelberg, N.Y. (1979); Ducheyne, P., "The fixation of permanent implants: a functional assessment", Function Behavior of Orthopaedic Biomaterials, Vol. II, CRC Press, Boca Raton, Fla. (1984).

Cementless fixation methods are not free from limitations. When porous coated devices are used the device is not permanently fixed at the time of surgery. A finite time is needed for bone tissue to develop in the porous coating interstices and eventually create sufficient fixation for patients to use their reconstructed joints fully.

It is known that bioactive materials such as calcium phosphate ceramics (CPC) provide direct bone contact at the implant-bone interface and guide bone formation along their surface. These effects are termed collectively osteoconduction. See, Gross, V., Schmitz, H. J., Strunz, V., "Surface Activities of bioactive glass, aluminum oxide, and titanium in a living environment. In: "Bioceramics: material characteristics versus in vivo behavior", Ed P. Ducheyne, J. Lemons, Ann. N.Y. Acad. Sci., 523 (1988); R. LeGeros et al., "Significance of the porosity and physical chemistry of calcium phosphate ceramics biodegradation-bioresorption", In: "Bioceramics: material characteristics versus in vivo behavior", Ed P. Ducheyne, J. Lemons, Ann. N.Y. Acad. Sci., 523 (1988). This property of bioactive ceramics is attractive, not only because it may help in averting long term bone tissue resorption, but also because it enhances early bone tissue formation in porous metal coatings such that full weight bearing can be allowed much sooner after surgery. Calcium phosphate ceramics, although widely known to be bone conductive materials, do not, however, have the property of osteo-induction, since they do not promote bone tissue formation in non-osseous implantation sites The enhancement of bony ingrowth was first documented with slip cast coatings Ducheyne, P., Hench, L. L., "Comparison of the skeletal fixation of porous and bioreactive materials", Trans. 1st Mtg. Europ. Soc. Biomater, p. 2PS, Sept. 1977, Strasbourg; Ducheyne, P., Hench, L. L., Kagan, A., Martens, M., Mulier, J. C., "The effect of hydroxyapatite impregnation on bonding of porous coated implants", Trans. 5th annual mtg., Soc. Biomat. p. 30 (1979); Ducheyne, P., Hench, L. L., Kagan, A., Martens, M., Burssens, A., Mulier, J. C., "The effect of hydroxyapatite impregnation on skeletal bonding of porous coated implants", J. Biomed. Mater. Res 14, 225–237 (1980). A porous stainless steel fiber network was coated with a slip cast CPC lining, and a marked increase of bone ingrowth was observed in comparison to the same porous metal without the CPC lining. This effect was pronounced at 2 and 4 weeks, but had disappeared at 12 weeks, because the slower full ingrowth without CPC lining had achieved the same level of ingrowth as that of the earlier extensive ingrowth caused by the osteoconductive lining.

Subsequently, the effect was studied mostly with plasma sprayed coatings, by numerous researchers. The studies to date, with the exception of one, have confirmed the beneficial effect of calcium phosphate based ceramic linings See, J. L. Berry, J. M. Geiger, J. M. Moran, J. S. Skraba, A. S. Greenwald, "Use of tricalcium phosphate or electrical stimulation to enhance the bone-porous implant interface", J. Biomed Mater. Res. 20, 65–77 (1986); H. C. Eschenroeder, R. E. McLaughlin, S. I. Reger, "Enhanced stabilization of porous coated metal implants with tricalcium phosphate granules", Clin. Orthop. 216, 234–246 (1987); D. P. Rivero, J. Fox, A. K. Skipor, R. M. Urban, J. O. Galante, "Calcium phosphate-coated porous titanium implants for enhanced skeletal fixation", J. Biomed. Mater. Res. 22, 191–202 (1988); M. D. Mayor, J. B. Collier, C. K. Hanes, "Enhanced early fixation of porous coated implants using tricalcium phosphate", Trans. 32nd ORS, 348 (1986); Cook, S. D., Thomas, K. A., Kay, J. F., Jarcho, M., "Hydroxyapatite-Coated porous titanium for use as an orthopaedic biologic attachment system", Clin. Orthop 230, 303-312 (1988); H. Oonishi, T. Sugimoto, H. Ishimaru, E. Tsuji, S. Kushitani, T., Nasbashima, M. Aona, K. Maeda, N. Murata, "Comparison of bone ingrowth into Ti-6Al-4 V beads coated and uncoated with hydroxyapatite", Trans. 3rd World Biomat Conf., Kyoto, p. 584 (1988). Yet, the magnitude of the effect has varied from study to study, and was not as pronounced as in an experiment performed by the present inventor. See, Ducheyne, et al., "The effect of hydroxyapatite impregnation . . . ", supra. More recently, it has been found that porous titanium, spherical bead coatings, plasma sprayed with two calcium phosphate powders (either hydroxyapatite or beta-tricalcium phosphate before spraying) also did not yield a clinically meaningful effect. See, Ducheyne, P., Radin, S., Cuckler, J. M., "Bioactive ceramic coatings on metal: structure property relationships of surfaces and interfaces", "Bioceramics 1988" Ed. H. Oonishi, Ishiyaku Euroamerica, Tokyo (1988 in press).

The variability of the effect among the studies noted suggests materials and processing induced parametric influences. The extensive characterization of some plasma sprayed coatings has unveiled that considerable changes of the physical and chemical characteristics of the ceramic subsequent to the deposition are possible. Specifically, differences in chemical composition, the trace ions present, the phases and their crystal structure, macro- and micro-porosity in the ceramic film, specific surface area, thickness, size and morphology of the pores and of the porous coating itself, and the chemical characteristics of the underlying metal may have occurred among the various studies Much of the prior art teaches the use of plasma spray techniques to form ceramic coating. Limitations of plasma spray coatings include: possible clogging of the surface porosity, thereby obstructing bone tissue ingrowth; difficulty in producing a uniform coating—although the HA can flow at the time of impact, plasma spraying is still very much a line of sight process, thus, it is not possible to coat all surfaces evenly, and certainly not the deeper layers of the coating, or the substrate; and finally if viscous flow is wanted, high temperatures are reached by the powders and uncontrolled, and thus unwanted transformation reactions can occur. Efforts to avoid these transformation reactions can be successful by minimizing the time of flight. However, a low intensity of viscous flow will result from this and thus, incomplete coverage of the metal can be the result. Thus, at present, it is difficult to obtain an optimal end-product, however, improved ceramic powders may overcome these limitations and provide useful coatings using plasma spraying techniques.

Figure 1:
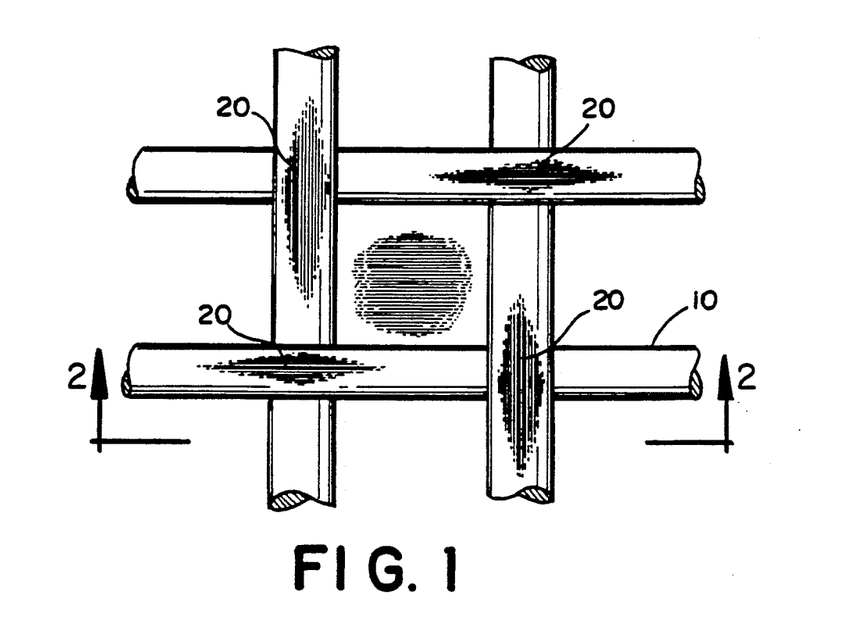
FIG. 1 is a top view of a portion of porous metal mesh which has an insufficient coating of calcium phosphate ceramic deposited by electrophoresis using materials and processes other than those disclosed.
Figure 2:
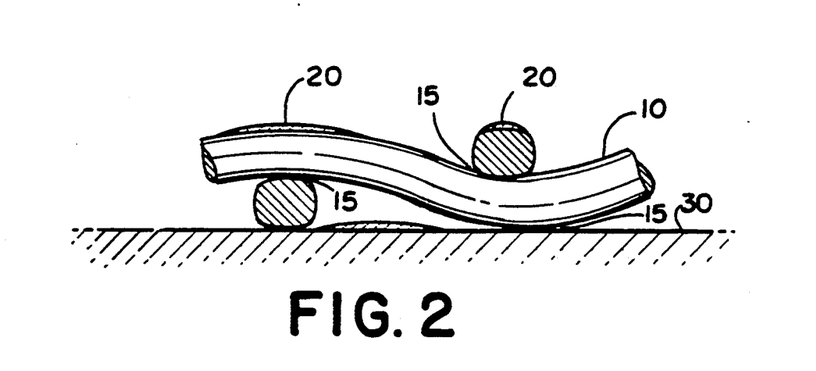
FIG. 2 is a cross sectional view of the porous metal mesh of FIG. 1.

The search thus continues for the optimal characteristics of the ceramic and for a process by which calcium phosphate ceramics may be deposited upon porous metal surfaces in a uniform manner and with predictable results. Although it is possible to coat flat plates of metals such as titanium by electrophoretic deposition, actual experiments by the applicants to deposit a uniform ceramic film on porous titanium using the information available prior to the current invention were unsuccessful. Referring to FIG. 1 and FIG. 2, there is illustrated a portion of a porous metallic device which is comprised of a woven mesh. Analysis of porous metallic devices with failed ceramic coatings showed that the ceramic particles were deposited primarily in the few areas indicated in FIG. 1 and FIG. 2. It is apparent that only those areas that were well exposed to the flow of particles were covered. During electrophoresis, the particles are electrically attracted to the metal; with a finite amount of particles in the solution, the particles will migrate first to the most accessible areas 20 of the metallic device 10, such as the tops of the wires. Further, some particles will be able to cross the potential field created by the wires if the particles are sufficiently far from each of the wires and be deposited on the substrate 30 to which the woven mesh is affixed. However, very few particles actually overcome this combination of attractive forces and adhere to the interstitial areas 15. Thus, the known electrophoretic process to coat flat titanium plates does not provide an adequately coated device.

Therefore, it can be seen that there remains a long felt, yet unfulfilled need for both a material with optimum characteristics and a deposition process which will allow uniform deposition of ceramic materials in a repeatable and commercially viable manner.

SUMMARY OF THE INVENTION

The present invention provides products and methods for enhancing the calcification phase of bone tissue growth. Since the calcification phase is a rate-limiting step of the reactions leading to bone tissue formation, the enhancement of calcification also enhances overall bone growth rates. Thus, the present invention provides materials and processes whereby calcification in porous coated bone implants is enhanced.

It has now been found that by using powdered calcium phosphate of sufficiently small particle size and of selected compositions, substantially improved coating materials result Moreover, by using a lower voltage potential, and commensurately, a longer deposition time cycle, uniform calcium phosphate films of acceptable thickness and quality may be electrophoretically deposited. In order to prevent agglomeration of the small particles while in solution, the process of the present invention utilizes ultrasonic agitation during the deposition process.

The size of the particles used to practice the present invention is critical As particle size is decreased, its ability to travel and adhere to the interstices improves. Also, if the weight concentration of the particles in solution is kept constant, then a larger quantity of particles is available and proportionately, more will remain in suspension and migrate into the interstices. The calcium phosphate powder of the present invention uses particles with a mean diameter of about $1 \times 10^{-6}$ to $5 \times 10^{-6}$ meters. The small particle size leads to the problem of agglomeration, both in the powdered form prior to mixing in solution and by the formation of clusters in solution. It is necessary therefore, to subject the solution to ultrasonic agitation immediately upon mixing, and to maintain this agitation during the electrophoretic deposition.

The deposition process of the present invention discloses optimal ranges for several parameters which must be controlled Specifically, electric potential gradients between 45-90 V/cm, and most preferably of 90 V/cm are disclosed Previously, preferably much higher gradients between 105-150 V/cm had been used for flat plate deposition. When the electric potential gradient is reduced, the time of deposition must be increased to achieve a sufficient thickness in the deposited film. However, the time for depositing layers between $20$–$80 \times 10^{-6}$ meters by the process disclosed is less than 60 seconds at the highest potential gradient of the range disclosed, i.e., 90 V/cm and using the porous mesh coatings of FIG. 1. Such conditions are considered acceptable for most commercial applications.

The preferred coating created in accordance with the present invention may also be subsequently sintered. The small particle size used results in shrinkage occurring during sintering, thereby leading to exposure of the underlying metal if the coating is too thin. For this reason, a minimum thickness for uniform ceramic coatings subsequent to sintering of $5 \times 10^{-6}$ meters and preferably of $20 \times 10^{-6}$ meters is disclosed.

The coatings achieved by the present invention, using ultrasonic agitation during the deposition process, provide a consistent electrophoretic yield from deposit to deposit, and also provide a great number of coatings for a given suspension bath. This advantage provided by the present invention results in a considerable increase in production efficiency and economic viability. The solution of the present invention lacks the agglomerations typically present; these large clusters do not remain in suspension and thereby substantially limit the number of films which may be deposited from one suspension. Previously, no more than 3 uniform depositions on flat titanium could be made. The presence of agglomerations in the prior art process reduces the amount of smaller particles available for deposition in a given solution concentration by weight, these few small particles are then used rapidly, and the solution must be replaced frequently in order to continue further deposition.

The present invention also provides novel electrophoretic coatings, which consist essentially of oxyhydroxyapatite and alpha- and beta-tricalcium phosphate, and which are essentially free of tetracalcium phosphate. By not heat treating in air (calcination) the calcium phosphate powder used and also by using a calcium-deficient hydroxyapatite with a limited amount of adsorbed water, substantially improved coatings are achieved. Normally, if calcium deficient hydroxyapatite is calcined prior to electrophoresis and subsequently sintered, tetracalcium phosphate is formed. This compound is unwanted since it is much too stable and will therefore not enhance bone ingrowth significantly. The present invention avoids the formation of tetracalcium phosphate and obtains oxy-hydroxyapatite, and alpha- and beta-tricalcium phosphate, which is highly desirable. It has also been found that it is preferable that the calcium deficient powder contain less than about 5% by weight of adsorbed water; if the water content is higher, electrophoretic deposition is highly ineffective in the non-aqueous suspension used in the present invention.

It is therefore an object of the present invention to create CPC materials which are useful in hard tissue reconstruction as materials which enhance bone tissue calcification.

It is a specific object of the present invention to provide easily reproducible, porous coated metal devices and which have uniform CPC coatings It is another object of the present invention to provide ceramic materials which will enhance bone formation in joint replacement devices.

Other objects will become apparent from the following description.

DETAILED DESCRIPTION

The present invention provides ceramic materials and the process for making them which enhance calcification to a greater degree than any other previously known ceramic coatings.

The approach taken contradicts the logic and thinking in the field of bioactive ceramics. The state-of-the-art of calcium phosphate ceramic coatings for enhancement of bone tissue ingrowth teaches the use of either hydroxyapatite (HA) coatings or beta-tricalcium phosphate coatings or a combination of both. It does so in view of the relatively high stability of the HA or the perceived slow degradability of beta-TCP. HA is considered stable and it is desired to be stable since it is used as a coating on dense, non-porous coated prostheses in which the HA coating serves as a permanent attachment vehicle. The state-of-the-art also teaches plasma spray deposition. It has now been found, however, that the choice of these materials, by themselves or in combination with plasma spraying is a poor choice. Stable or slowly degrading materials or coatings have been found to be sub-optimal. Instead, the present invention teaches the use of materials and coating with the highest dissolution rate as measured by the release of calcium.

The materials of the present invention are unstable Ca—(PO$_4$) compounds that are a microscopic mixture of electrophoretically formed CA—P type materials and not a physical mixture of powders of different Ca—P type materials; in addition, they have a specific surface area which, in the case of coatings, exceeds 1 m$^2$/g. Separately, hydroxyapatite, oxy-hydroxyapatite, alpha- and beta-tricalcium phosphate do not have a high dissolution rate; however, when formed by electrophoresis and subsequently sintered in a microscopic mixture, the resulting dissolution rate increases by ten fold. This result is particularly surprising since the HA, oxy-HA, alpha- and beta-TCP are powders, and it would be expected by those of ordinary skill to have a higher dissolution rate since powders have a much greater exposed surface area than coatings.

The present invention provides a novel prosthetic surface for implantation in bony tissue comprising a porous titanium substrate uniformly coated with a coating consisting essentially of oxyhydroxyapatite, alpha-tricalcium phosphate (hereinafter Alpha-TCP) and beta-tricalcium phosphate (hereinafter beta-TCP). The porous metal devices that were used to reduce part of the invention to practice are made using orderly oriented wire mesh (OOWM) porous metal coatings, see P. Ducheyne, M. Martens, P. De Meester, J. C. Mulier, "Titanium implants with porous structure for bone ingrowth: a general approach", "Titanium and Its Alloys for Surgical Implants", ed. H. A. Luckey, ASTM, Philadelphia, Pa., 1983; P. Ducheyne, M. Martens, "Orderly oriented wire meshes (OOWM) as porous coatings on orthopaedic implants", I Morphology, J. Clin. Materials, 1 59-67, (1986); P. Ducheyne, M. Martens, "Orderly oriented wire meshes (OOWM) as porous coatings on orthopaedic implants; II: the pore size, interfacial bonding and microstructure after pressure sintering of titanium OOWM", J. Clin. Materials, 1, 91-98 (1986); the method that was used to prepare some of the coatings or powders of the current invention was electrophoretical deposition of CPC films followed by sintering, see, Ducheyne, P., Van Raemdonck, W., Heughebaert, J. C., Heughebaert, M., "Structural analysis of hydroxyapatite coatings on titanium", Biomaterials 7, 97-103 (1986), which are hereby incorporated by reference.

Figure 3:
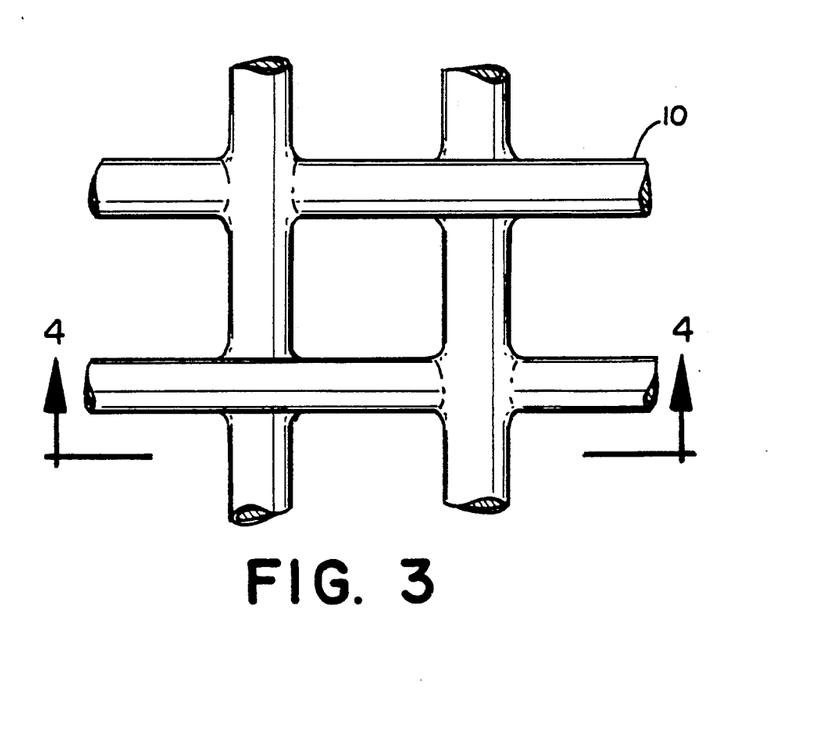
FIG. 3 is a view of a mesh similar to FIG. 1, but coated in accordance with present invention.
Figure 4:
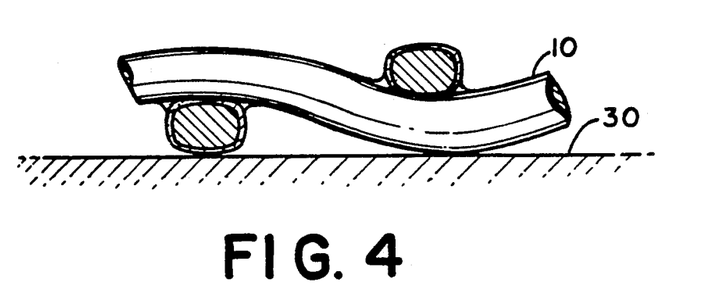
FIG. 4 is a cross sectional view of the coated mesh of FIG. 3.

Referring to FIG. 3 and 4, it can be seen that the methods of the present invention result in a ceramic coating which covers substantially all exposed surfaces of the metallic device 10. One of ordinary skill will realize that FIGS. 2 and 3 are generalized representations, not made to any scale. Thus, the methods of the present invention and the ceramic materials disclosed permit porous surfaces, such as the woven wire mesh shown to be electrophoretically coated with a calcium phosphate ceramic material.

Preparation of Coatings

For comparative purposes, a number of different types of coatings were created using the following procedures. CPC powders are either obtained commercially or synthesized Referring to Table 1, the HA-1 powder is a "Calcium Phosphate Tribasic" (Merck, Darmstadt, Germany) This powder is identical to the HA-1 disclosed previously, see, Ducheyne, P., Van Raemdonck, W., Heughebaert, J. C., Heughebaert, M., "Structural analysis of hydroxyapatite coatings on titanium", Biomaterials 7, 97-103 (1986), which is hereby incorporated by reference. Hydroxyapatite HAp-1 and HAp-2, and tricalciumphosphate apatitic-TCP (ap-TCP) and beta-TCP may be synthesized according to procedures disclosed previously, see, Bonel, G., Heughebaert, J. C., Heughebaert, M., Lacout, J. L., Lebugle, A., "Apatitic Calcium Orthophosphates and related compounds for biomaterials preparation", In Bioceramics: "Material Characteristics vs. in vivo behavior", Ed P. Ducheyne, J. Lemons, Ann. N.Y. Ac. Sci., 523 (1988), which are hereby incorporated by reference. The two numbers of HAp refer to two different lots.

The powders used and some of their characteristics are summarized in Table 1. The X-ray diffraction (XRD) patterns may be determined using, for example, a Rigaku diffractometer with Cu—K alpha radiation at 45 kV, 35 mA, a scanning rate of 1° 2(theta)/min. and a computerized diffractogram analyzer.

The infrared spectrum is obtained using a Fourier transform infrared spectroscope (FTIR) (Nicolet 5 D×C). Spectra were recorded on 1% powder-KBr mixtures in the diffuse reflectance operational mode.

A calcination, which, however is not wanted or necessary to make the ceramic products of the present invention, typically for 1 hour at 900° C. in air, was performed on some of the powders used for comparison purposes. One of the effects of this step is to substantially remove adsorbed water.

The porous coated specimens used to generate the accompanying data were Ti-6Al-4 V alloy plates, $3 \times 10 \times 10$ mm, with a commercial purity (c.p.) Ti, orderly oriented wire mesh pressure sintered as described previously, see, P. Ducheyne, M. Martens, "Orderly oriented wire meshes (OOWM) as porous coatings...", supra. The wire mesh was a 16 mesh size twill weave of 0.50 mm diameter wire, Id. The composition of the Ti alloy plate fell within the specifications of ASTM standard F-136. Prior to the electrophoretic deposition, the metal specimens were ultrasonically cleaned in acetone, immersed for 10 sec. into a 2% HF+20% HNO$_3$ aqueous solution, and subsequently rinsed in distilled water.

The CPC coatings were electrophoretically deposited from a 3% suspension of the powders in isopropanol. A 10 mm distance between the lead anode and the cathodic metal specimen was used. The electrophoretic yield on dense or porous coated metal substrates was determined for electrical fields between 60 and 100 V/cm and time of deposition from 10 to 60 sec. Before applying the voltage, the suspensions were ultrasonically stirred in order to break the powder particle clusters. All metal substrates were weighed prior to and subsequent to the deposition process.

Any thermal treatment of the CPC subsequent to electrophoresis, was carried out in vacuum and at relatively low temperatures, in order to minimize the effect on the mechanical properties of the underlying metal. Typical parameters were 925° C., 2 hours, $10^{-6}$ to $10^{-7}$ torr and FTIR characterization studies subsequent to deposition and sintering, if any, were made on either the deposited coatings or scraped off powders respectively.

In view of their intended in vivo use, the assessment of stability in simulated physiological solutions was determined first. Specifically, a solution devoid of calcium and phosphate ions, i.e., a 0.05 M tris-(hydroxy)-methylaminomethane—HCl buffered solution (pH-7.3 at 37° C.), was chosen and both the dissolved calcium and the weight loss due to debonding of the coating as a function of immersion time were measured The CPC coatings were obtained starting from HA-1 powder exclusively. The coatings were deposited at 90 V for 60 sec. A 1 mg/1 ml coating weight to solution volume was used, i.e., specimens with a 10 mg coating were immersed in 10 ml of solution contained in 23 mm diameter polystyrene vials The vials were placed onto a shaker in a water-jacketed incubator. For each time of immersion four separate specimens were used. As controls, solutions without specimens and solutions with as received HA-1 powder were used. Similarly, four samples were used for each immersion time. At the end of each immersion time, the specimens were dried and weighed immediately.

The amount of calcium eluted from each of the specimens was measured in triplicate by flame atomic absorption spectroscopy (AAS). Standard solutions of 0.1, 0.5, 1, 2, 5, and $10 \times 10^{-3}$ mg/ml of calcium were made from a 1,000 mg/ml stock solution of calcium with 1% by weight of lanthanum chloride.

The specific areas of the powders and CPC coatings on porous Ti used were measured by the B.E.T. technique on a Quantasorb, Quantachrome instrument (Greenvale, N.Y.). The morphology of the powders, and the coatings prior to and as a result of the immersion tests was analyzed using scanning electron microscopy (Philips SEM 500, Eindhoven, The Netherlands). All powders, including those used for comparative purposes only and which are not an object of the present invention were prepared for S.E.M. analysis by suspending them ultrasonically in the isopropanol solution (5 mg/30 ml isopropanol). A droplet of the suspension subsequently was dripped onto the polished aluminum SEM-specimen holder. This technique allowed the powders to be visualized as particles the way they were in solution, and not as clusters that these particles usually form.

The characteristics of the various powders, some of which were only used for comparative purposes, are summarized in Table 1. The Ca/P atomic ratio was determined by X-Ray diffraction. The specific surface area values were either measured before or determined for other syntheses using identical synthesizing procedures.

As indicated in Table 1, the Ca/P ratios of HA-1, HAP-1 and -2, and TCP were 1.61, 1.67, 1.67 and 1.47 respectively Thus HA-1 is a Ca-deficient, non-stoichiometric apatite, corresponding to the formula $Ca_{10-x}$ $(HPO_4)_6$ $(OH)_{2-2x}$. The HAp-1 and -2 has a perfect hydroxyapatitic stoichiometry and therefore is used to assess the effects of a departure from stoichiometry associated with HA-1. The Ap-TCP powders were used in view of the combination of an apatitic structure with a TCP stoichiometry. The infrared spectra prior to and after calcination of HA-1, HAp-1 and TCP further support the X-Ray diffraction identifications. A broad band is observed in the 3000–3600 $cm^{-1}$ range which is indicative of the stretching vibration of the hydroxyl ions in the adsorbed water, and peaks seen at 875, 1412 and 1455 $cm^{-1}$ are due to the presence of carbonate groups. Prior to calcination, the hydroxyl peaks at 630 and 3570 $cm^{-1}$ observed are small; however, they are considerably more intense after calcination. Furthermore, subsequent to calcination of HA-1, two characteristic peaks for beta-TCP were observed: 940 and 970 $cm^{-1}$. Thus the calcination produces a full crystallization of the hydroxyapatite and a partial transformation to beta-TCP in HA-1.

The infrared spectra of HAp-1 indicate that it is a poorly crystallized apatite with a considerable amount of adsorbed water prior to, but a pure hydroxyapatite subsequent to, calcination. The IR spectrum prior to calcination shows a very small OH peak at 3570 $cm^{-1}$, a very strong $NO^{3-}$ band at 1390 $cm^{-1}$ and a broad band indicative of adsorbed water in the 3000–3600 $cm^{-1}$ range. Subsequent to calcination, the OH-peak appears larger, the $NO_3$ peak disappeared and the two bands at 1040 and 1090 $cm^{-1}$ specific for the nu-3 stretching vibrations of the $PO_4$ group in hydroxyapatite have become distinct. Thus, in conjunction with the X-Ray diffraction data, the infrared results indicate that HAp-1, calcined, is a well crystallized stoichiometric anhydrous hydroxyapatite.

The infrared spectrum of the TCP shows it is a poorly crystallized apatic structure prior to heating. There is a broad band indicative of adsorbed water in the 3000 to 3600 $cm^{-1}$ range. The subsequent calcination step produces the strong peaks at 940 and 970 $cm^{-1}$ characteristic of beta-TCP. Yet, there are also traces of beta-$C_2P_2O_7$ as revealed by the small peaks or shoulders at 570, 725, 1026, 1106, 1187 and 1212 $cm^{-1}$.

A comparative analysis of the electrophoretic yield, i.e., whether or not CPC powders can be electrophoretically deposited follows from Table 2. This table summarizes the coating weight or one condition of electrophoresis (100 V/cm for 60 sec.)[1] for all dissimilar powders of the study, i.e., HA-1, HAp-1 and Ap- or beta-TCP. Table 2 also represents the water content and the current density during the electrophoresis. It follows from this table that both HAp-1, non calcined and Ap-TCP, which is also a non-calcined powder, cannot be deposited. The weight of the deposit is virtually zero. Calcination produces, among other effects, the elimination of the adsorbed water. Subsequent to this heat treatment both powders can be deposited, as is indicated by the coating weight. Since irrespective of composition or crystal structure, deposition is both possible or excluded, it would therefore follow from these data that the adsorbed water interferes with the electrophoretic transport. Yet the HA-1 powder contains some adsorbed water and, as shown in Table 1, it does electrophorectically deposit. Thus, there is a critical concentration of adsorbed water above which electrophoretic deposition is not possible This critical value is probably about 5%, considering that the non-stoichiometric HA-1 powder can still be deposited with a 4.8% water content. With too high a water content the adsorbed water becomes sufficiently accessible at the particle surface immersed in the alcohol solution and the electric energy is consumed in a hydrolysis reaction and no longer in particle transport.

The electrical field used was chosen at the time of this experiment, prior to the determination of the optimal ranges disclosed elsewhere.

Specific surface areas varied by an order of magnitude among the powders that can be deposited (see Table 1). Therefore, this parameter does not appear to exert a predominant effect. Neither does the morphology of the particles affect the outcome of the electrophoretic deposition process substantially.

HA-1 powder was used to establish the relationship between the electrophoretic deposition parameters (time, voltage) and the coating thickness. A given thicknesses can be obtained in a shorter time when a higher voltage is applied. Obviously, porous coated surfaces required longer deposition times than smooth titanium specimens for similar deposit thicknesses. A uniform thickness of the deposit in the porous coating cannot be achieved with thin coatings ($<5 \times 10^{-3}$ mm) and with higher voltage gradients ($>105$ V/cm).

Table 3 summarizes the chemical compositions and crystal structures of the CPC powders and coatings for which HA-1 and HAp-1 were the starting powders. For the sake of convenience, some of the as-received characteristics reported above also are included in this table. The following symbols are used:

AR: as received
C: Calcination (900° C., 1 hour, air, furnace cooling)
ED: electrophoretic deposition (90 V/cm, 60 sec.)
VT: heat treatment in vacuum ($10^{-7}$ torr) without underlying Ti substrate (925° C., furnace cooling under vacuum); the subscript indicates the hours at temperature.
VS: sintering in vacuum ($10^{-7}$ torr) with an underlying Ti substrate (925° C., 2 hours, furnace cooling under vacuum)

When the pure hydroxyapatite is vacuum treated at 925° C. without an underlying Ti substrate the XRD pattern indicates it is a highly crystalline apatic structure. The analysis of the FTIR spectrum then indicates it is an oxyhydroxyapatite material. Specifically the nu-4 vibration of $PO_4$ in the 550–600 $cm^{-1}$ interval, and the absence of the weak presence of the 3570 $cm^{-1}$ and 630 $cm^{-1}$ OH-absorption bands provide strong evidence for the presence of a partially, if not nearly fully dehydroxylated apatitic structure $Ca_{10}$ $(PO_4)_6$ $(OH)_{2-2y}$ $O_y$ $[]_y$ with the symbol $[]$ representing a vacancy.

The time of vacuum treatment, i.e., 8 or 24 hours, does not yield a meaningful difference; qualitatively, the same structures are identified.

When the pure HAp (i.e., HAp1-C) is electrophoretically deposited onto the titanium substrate, removed from it, and heat treated (without an underlying Ti substrate) the structural findings do not change. That is, the electrophoretic deposition in isopropanol does not affect the structure of the CPC powder.

When the pure HAp (i.e., HAp1-C) is, however, deposited and vacuum sintered onto the underlying titanium substrate, it transforms to a mixture of oxyhydroxyapatite and tetracalcium phosphate. The latter phase is formed because the underlying titanium substrate easily attracts phosphorous. Therefore, with a reduced concentration of P, the Ca to P ratio increases from its initial value of 1.67, eventually resulting in a partial transformation to tetracalcium phosphate.

The structural and compositional changes that occur in CPC that are not pure hydroxyapatite do not necessarily differ from those occurring in the pure hydroxyapatite. This is in particular true when as the starting compound for electrophoresis, vacuum treatment or vacuum sintering a mixture of pure hydroxyapatite and some other compound is used. This can be done by using HA-1 in the calcined condition (HA-1 - C), since this powder is a mixture of pure hydroxyapatite and beta-tricalcium phosphate. Subjecting this powder to the same treatment, i.e., electrophoretic deposition and vacuum sintering, as the pure hydroxyapatite (HAp-1, C), produces the same qualitative transformations that is, the hydroxyapatite transforms to a mixture of oxyhydroxyapatite and tetracalcium phosphate. In addition, however, the presence of beta-tricalciumphosphate must be considered; and this compound partially transforms to alpha-tricalciumphosphate.

The ceramics and coatings of the present invention are generally unstable, do not have substantial amounts of tetracalciumphosphate, and exhibit high dissolution rates. They consist essentially of oxyhydroxyapitite, alpha-TCP and beta-TCP. Whereas sintering the commercially obtained CPC powder HA-1 in the calcined condition on titanium does not produce principally different results from the experimentation with pure hydroxyapatite (HAp-1), the eventual structure with the non-calcined commercial powder HA-1 diverge markedly, however, the mechanisms are still the same. HA-1, non-calcined, is a Ca-deficient hydroxyapatite. When vacuum treated on a titanium substrate, four concurrent effects take place. First, the effect of calcination itself, i.e., transformation of the Calcium deficient hydroxyapatite to a pure hydroxyapatite and beta-tricalcium phosphate mixture; second, the partial dehydroxylation of the hydroxyapatite to form oxyhydroxyapitite; third, the partial transformation of beta-TCP to alpha-TCP; and fourth, the preferential diffusion of P to the Ti substrate, thereby increasing the Ca to P ratio in the mixture. The first three effects are present in HA-1, AR, VT (i.e., without the underlying metal substrate) and thus the net effect is a transformation to a mixture of oxyhydroxyapatite, beta- and alpha-TCP, as follows from the XRD pattern and FTIR spectrum. Such phase transformation can also be achieved with other processes which subject calcium deficient hydroxyapatite to high temperature and to an atmosphere provoking full or partial dehydroxylation.

With the underlying Ti substrate the average Ca to P ratio of the coating increases from its original value of 1.61. Based upon the experimental observations, the ratio never reaches 1.67 or higher during sintering, since only oxyhydroxyapatite, and beta- and alpha-TCP is observed Thus, when the CPC coating has a Ca/P ratio prior to sintering of 1.67, the loss of P leads to a mixture of compounds, with a ratio of 1.67 and 2; when the ratio before sintering is below 1.67, e.g., 1.61 it is possible to still obtain a mixture of compounds with respective atomic ratios of 1.5 and 1.67 subsequent to vacuum sintering on titanium. One of ordinary skill in the art will realize that the effect of the underlying titanium on the desired phase transformation in the ceramic will occur regardless of the deposition process used, so long as the reaction time is sufficient and no other substances interfere with the phosphorous diffusion.

As was the case for the pure hydroxyapatite, the electrophoretic deposition does not change the characteristics of the powder: the XRD patterns of HA-1, AR prior to and/or after electrophoretic are identical.

In Vivo Experiments

In order to determine the effects of the various coatings described above on actual bone ingrowth, certain experiments were conducted. The experiments are best understood by referring to the data contained in Tables 4-6. The process of the present invention was carried out using a starting powder, HA1, which is a calcium deficient hydroxyapatite (Merck). CAP 1 is formed by making a composite of 75% HA1 and 25% poly(lactic acid) (% by weight). The composite is deposited by making a suspension in an easily vaporizable solvent (methylene chloride) and dipping a porous metallic specimen into it. CAP 2 is a film formed by electrophoretic deposition. The film is $75 \times 10^{-6}$ meters thick; the deposition process occurred at a potential of 90 V/cm for 60 seconds. CAP 3, a sintered material, was formed using CAP 2 material. The sintering occurred in a vacuum ($10^{-6}$ torr, at 925° C. for 2 hours. The type, thickness and other parameters associated with each coating is contained in Table 6, as well as the initial in vitro dissolution rate for each coating.

The results illustrated in Tables 4-6, were obtained using rectangular plugs $10 \times 5 \times 5$ mm, possessing an orderly oriented cp (commercial purity) Ti mesh surface coated with the three calcium phosphate films described above: CAP 1, CAP 2, and CAP 3; an uncoated plug served as a control. In vitro dissolution rates were determined by immersion in 0.05 M tris physiologic solutions for periods of time ranging from 5 minutes to 24 hours. Table 4 reports the dissolution rates observed. In accordance with the present invention, the coating formed should be relatively unstable. Dissolution rates are an indication of that instability when exposed to physiologic solutions. Coatings of the present invention should exhibit initial dissolution rates under the experimental conditions described above in excess of $15 \times 10^{-7}$ mg/cm$^2$·sec, preferably about $60 \times 10^{-7}$ mg/cm$^2$·sec, as indicated for CAP 3 coating described in Table 5.

Thirty adult beagle dogs were equally divided into study periods of 2, 4 and 6 weeks. One of each type plug was press fit into the medial and lateral supracondylar region of both hind limbs. Each specimen was pull tested at sacrifice to determine the interfacial bonding. The decohesion and shear strengths and the levels of statistical significance among the various material types are contained in Tables 4 and 5. One of each type plug was press fit into the medial and lateral supracondylar region of both hind limbs according to a predetermined randomized order. Radiographs were taken pre- and post-operatively and at sacrifice. Each implant underwent mechanical pullout testing to determine ultimate shear strength. A randomized block ANOVA followed by a Student-Newman-Keuls test compared the groups. No implants became infected. On radiographic review, no lucencies were present at the bond/coating interface. Initial dissolution rates for CAP 1, CAP 2, and CAP 3 were $2.7 \times 10^{-7}$, $5.5 \times 10^{-7}$ and $6 \times 10^{-6}$ mg/cm²s respectively. Ultimate shear strength increased both over time and with increasing dissolution rates (see Table 4). The uncoated mesh strengths were 2.7, 3.3. and 3.6 MPA for the 2, 4 and 6 week time periods CAP 1 strengths were 2.1, 2.8 and 4.2 MPA which were not statistically different from the uncoated mesh. CAP 2 strengths were 3.6, 4.8 and 5.2 MPA. CAP 3 strengths were 4.1, 5.6 and 6.6 MPA. At 6 weeks, the CAP 3 mesh was significantly stronger than the CAP 2 mesh.

As seen from Tables 4-6, the CAP 3 coating, which has the highest dissolution rate, also promotes the best mechanical bond. This dissolution of the coating acts by providing a local source of ions essential for tissue calcification. The CAP 3 coating is also quite uniform and complete, having been deposited in accordance with the preferred processing parameters discussed above (and used for the comparative coatings as well). The CAP 1 coating is not acceptable, since it results in lower initial bonding strength compared to the porous metal coating without the ceramic used as a control. The CAP 2 coating is acceptable and demonstrates the advantages of using the preferred embodiment coating method.

As seen from the above, superior prosthetic surfaces are achieved by using porous titanium coatings which are uniformly coated with ceramic films of specific composition, under controlled deposition procedures.

The resulting CAP 3 films are relatively unstable, having higher dissolution rates which result from the fact that they are essentially free of tetracalcium phosphate, and instead consist essentially of alpha and beta tricalcium phosphate, and oxyhydroxyapatite.

While the present invention has been described in connection with prothesis implantation, other major applications of the calcification enhancement materials of the present invention is bone augmentation. A press fit prosthesis needs to attract calcified tissue as quickly as possible in those areas where bone is not present. This absence of bone can be the result of surgical destruction or of prior bone trauma. In the mandibula or the maxilla, loss of bone mass follows from full or partial loss of dentition. The bone can be rebuilt with calcification promoting substances. Such rebuilding can be undertaken without, or alteratively with proteins that are derived from bone tissue Such proteins can be made in larger quantities by genetic engineering techniques if necessary. Such proteins may trigger the formation of the organic matrix of bone in non bone-tissue sites. Thus, when the underlying pathology is such that the bone metabolism is seriously affected, a trigger is needed, supplemented with a substance that enhances the calcification and the overall rate of bone formation. These instances can be situations of larger mandibular or maxillar bone loss, due either to pathology (cysts), absence of dentition, filling of extracted tooth root sites or periodontal lesions. Additional applications for the combined use of biological growth factors and calcium phosphate ceramics are conditions of traumatic bone loss and the absence of normal healing processes like in non-unions. Yet another application could be the surgical repair of osteoporotic bone loss and concomitant bone collapse. Thus, those of ordinary skill in the art will recognize that the ceramic coatings of the present invention can be removed from the underlying metallic substrate on which they are formed, and be injected in powdered form or otherwise introduced into proximity with bony tissue, to substrate on which they are formed, and be injected in powdered form or otherwise introduced into proximity with bony tissue, to promote its growth.

TABLE 1

| | | Characteristics of the starting CPC powders | | | | | |
|---|---|---|---|---|---|---|---|
| Denomination | Synthesis | Chemical formula | Ca/P ratio | Water content % (by wt.) | $NO_3^{2-}$ content % (by wt.) | $CO_3^{2-}$ content % (by wt.) | SSA m²/g |
| HA1 AS rec'd | $P^x$ | $Ca_{10-x}(HPO_4)_{6-y}(OH)_{3-x}$ | 1.61 | 4.8 | — | 1.5 | 76.0 (ref. 24) |
| HA1$_c$ (calcined) | $P^x + C^{xxx}$ | HA + β-TCP mixture | " | — | — | — | n.d. |
| HAP1 | $P^x + L^{xxx}$ | $Ca_{10}(PO_4)_6(OH)_2$ | 1.67 | 9.9 | — | — | 42 (ref. 24, 26) |
| | $P + L + C^{xxx}$ | $Ca_{10}(PO_4)_6(OH)_2$ | " | 0 | | | 3.7 (ref. 26) |
| HAP2-A | $P + L$ | $Ca_{10}(PO_4)_6(OH)_2$ | 1.67 | 15.6 | ... | — | — |
| AP-TCP | $P + L$ | $Ca_9(HPO_4)(PO_4)_5OH$ | 1.47 | 11 | — | — | 64 (ref. 26) |
| β-TCP | $P + L + C$ | $Ca_9(PO_4)_6$ + traces β-$Ca_2P_2O_7$ | | 0 | — | — | 4. 4. (ref. 26) |

$P^x$ - precipitation
$L^{xx}$ - lyophilization
$C^{xxx}$ - calcination 900° C., 1 hr, 01iL
n.d.: not determined

TABLE 2

Electrophoretic deposition results for various CPC powders deposited at 100 V/cm for 60 sec.

| Powder | Water Content % (by weight) | Current density + (mA/cm²) | Coating weight (mg/cm²) |
|---|---|---|---|
| HA1 (nc*) | 4.8 | 15-30 | 10 ± 2 |
| HAp-1 (nc*) | 9.9 | >1000 | 0 |
| HAp-1 (c**) | 0 | <20 | 10 |

TABLE 2-continued

Electrophoretic deposition results for various CPC powders deposited at 100 V/cm for 60 sec.

| Powder | Water Content % (by weight) | Current density+ (mA/cm$^2$) | Coating weight (mg/cm$^2$) |
|---|---|---|---|
| Ap-TCP (nc*) | 11 | 19–21 | 0 |
| β-TCP (c**) | 0 | <15 | 15 |

Notes:
*nc: non-calcined
**c: calcined
+: the current density decreases during deposition, therefore only a range is indicated

TABLE 3

Characteristics of the treated CPC powders and coatings.

| Base powder | treatment | structural characteristics |
|---|---|---|
| HAp-1 | AR (precip and lyophilized) | poorly crystalized hydroxyapatite (single phase material) |
| HAp-1 | AR + C | pure hydroxyapatite (single phase material) |
|  | AR + C + VT$_8$ | oxyhydroxyapatite (single phase material) |
|  | AR + C + VT$_{24}$ | oxyhydroxyapatite (single phase material) |
|  | AR + C + ED + VS | oxyhydroxyapatite, tetracalciumphosphate |
| HA1 | AR + C | hydroxyapatite(HA) + β-tricalcium - phosphate(β-TCP) (two phase material) |
|  | AR + C + ED + VS | oxyhydroxyapatite + tetra-calciumphosphate + α-TCP |
| HA1 | AR | Ca-deficient hydroxyapatite (one phase material) |
|  | AR + ED | Ca-deficient hydroxyapatite (same as AR) |
|  | AR + VT$_2$ | oxyhydroxyapatite with traces of α-, β-TCP |
|  | AR + ED + VS | oxyhydroxyapatite with α-, β-TCP + — |

TABLE 4

| Ceramic coating | initial in vitro Ca dissolution rate (10$^7$ × mg/cm$^2$.s) | in vivo interfacial 2 wks | decohesion shear strength (MPa + S.D.) 4 wks | 6 wks |
|---|---|---|---|---|
| name: (porous metal only) | — | 3.80 (1.44) | 3.34 (0.46) | 3.61 (0.72) |
| CAP 1 | 2.7 | 2.17 (0.96) | 2.83 (0.19) | 4.26 (0.32) |
| CAP 2 | 3.7 | 3.38 (1.00) | 4.83 (0.49) | 3.24 (0.72) |
| CAP 3 | 10.0 | 4.13 (1.43) | 3.82 (8.44) | 6.82 (0.86) |

TABLE 5

| Pairs | Time of implantation (weeks) 2 | 4 | 6 |
|---|---|---|---|
| no coating |  |  |  |
| vs CAP 1 | <0.2 | <0.2 | <0.5 |
| CAP 2 | 0.1 | 0.05 | 0.05 |
| CAP 3 | 0.005 | 0.01 | 0.001 |
| CAP 1 |  |  |  |
| vs CAP 2 | 0.005 | 0.002 | 0.1 |
| CAP 3 | 0.001 | 0.001 | 0.001 |
| CAP 2 |  |  |  |
| vs CAP 3 | 0.2 | 0.2 | 0.05 |

TABLE 6

| | initial in vitro dissolution rate ($10^{-7}$ · mg · cm$^{-2}$ · sec$^{-1}$) | in vitro coating degradation (%) | coating composition | thickness (mm) | specific surface area (m$^2$/g) |
|---|---|---|---|---|---|
| CAP 1 | 2.7 | 0.2 | poly (lactic acid)-calcium deficient apatite composite | 50 | / |
| CAP 2 | 5.5 | 82.7 | calcium deficient apatite | 75 | 85.0 |
| CAP 3 | 60 | 13.3 | oxyhydroxyapatite, α- and β TCP | 75 | 9.2 |

*- coating weight loss due to particle release after 1 hr. of immersion

What is claimed is:

1. A method of depositing a highly soluble bone tissue activation material upon the porous metallic substrate surface of a bone implant device, comprising the steps of:

(a) combining a calcium deficient hydroxyapatite powder which contains approximately less than about 5% by weight of adsorbed water and a non-aqueous liquid to form a suspension;

(b) agitating said suspension to deglomerate said powder;

(c) immersing the substrate into said suspension;

(d) depositing a calcium phosphate film on said substrate by low voltage electrophoresis to form a uniform coating in thickness on all surfaces of the substrate whereby said thickness is at least 5 microns which, after implantation, enhances bone tissue growth into said device.

2. The method of claim 1, further comprising the step of:

(e) sintering the calcium phosphate coated porous substrate in a vacuum.

3. The method of claim 2, said sintering being conducted at a vacuum of less than about $10^{-4}$ torr and at temperatures between about 800° and 1300° C.

4. The method of claim 3, wherein said porous metallic substrate is comprised of titanium and said sintering is conducted at temperatures below about 975° C.

5. The method of claim 2, wherein said powder is selected and agitated to provide said calcium phosphate powder particles in suspension having diameters between about $0.5 \times 10^{-6}$ and $10 \times 10^{-6}$ meters.

6. The method of claim 2, wherein said powder is selected and agitated to provide said calcium phosphate powder particles in suspension having diameters between about $1 \times 10^{-6}$ and $7 \times 10^{-6}$ meters.

7. The method of claim 2, wherein said powder is selected and agitated to provide said calcium phosphate powder particles in suspension having diameters between about $1 \times 10^{-6}$ and $5 \times 10^{-6}$ meters.

8. The method of claim 2, wherein said electrophoresis is carried out using a voltage gradient between about 45 and 90 volts/cm.

9. The method of claim 2, wherein said film is greater than about $5 \times 10^{-6}$ meters and less than about $150 \times 10^{-6}$ meters in thickness.

10. The method of claim 2, wherein said film is greater than about $20 \times 10^{-6}$ meters and less than about $80 \times 10^{-6}$ meters in thickness.

11. The method of claim 1, wherein said powder has not been calcinated.

12. The method of claim 2, wherein said porous substrate is comprised of a woven mesh.

13. The method of claim 2, wherein said agitation is carried out at a frequency greater than about 20,000 Hz.

14. A method of enhancing the bioactivity of a calcium phosphate ceramic material by avoiding the formation of tetracalcium phosphate, comprising the steps of:
   (a) combining a calcium deficient hydroxyapatite which has a limited amount of adsorbed water with a non-aqueous liquid to form a suspension;
   (b) electrophoretically depositing a calcium phosphate layer of uniform thickness on all surfaces of an object; and
   (c) sintering said layer.

15. The method of claim 14, wherein said hydroxyapatite has an adsorbed water content of less than about 5% by weight.

* * * * *

UNITED STATES PATENT AND TRADEMARK OFFICE
CERTIFICATE OF CORRECTION

PATENT NO. : 4,990,163
DATED : February 5, 1991
INVENTOR(S) : Paul Ducheyne; John Cuckler; Shulamit Radin It is certified that error appears in the above-indentified patent and that said Letters Patent is hereby corrected as shown below:

Column 1, before "Field of the Invention", please insert --

This work was supported in part by research grant number ECE-85 15031 from the National Science Foundation. The United States Government may have certain rights in this invention. --

Signed and Sealed this

Twenty-eight Day of March, 1995

Attest:

BRUCE LEHMAN

*Attesting Officer*    *Commissioner of Patents and Trademarks*